United States Patent [19]
Chen

[11] Patent Number: 6,120,287
[45] Date of Patent: Sep. 19, 2000

[54] APPARATUS AND METHOD FOR MEASURING ORTHODONTIC FORCE APPLIED BY AN ORTHODONTIC APPLIANCE

[75] Inventor: Jie Chen, Indianapolis, Ind.

[73] Assignee: Advanced Research and Technology Institute, Inc., Indianapolis, Ind.

[21] Appl. No.: 09/369,544

[22] Filed: Aug. 6, 1999

[51] Int. Cl.[7] .................................................. A61C 3/00
[52] U.S. Cl. ................................... 433/2; 433/24; 433/72
[58] Field of Search .................................. 433/2, 24, 56, 433/72, 196

[56] References Cited

U.S. PATENT DOCUMENTS

| | | |
|---|---|---|
| 3,349,489 | 10/1967 | Shackelford . |
| 3,533,163 | 10/1970 | Kirschenbaum . |
| 4,083,114 | 4/1978 | Acevedo . |
| 4,722,686 | 2/1988 | Salib . |
| 4,979,312 | 12/1990 | Wool ......................................... 433/72 |
| 4,983,120 | 1/1991 | Coleman et al. .......................... 433/24 |
| 5,028,232 | 7/1991 | Snow . |
| 5,055,041 | 10/1991 | Eckland . |
| 5,064,368 | 11/1991 | Lavin . |
| 5,100,316 | 3/1992 | Wildman ................................... 433/24 |
| 5,651,671 | 7/1997 | Seay et al. . |
| 5,752,832 | 5/1998 | Vardimon et al. . |
| 5,803,730 | 9/1998 | Khademazad et al. . |

OTHER PUBLICATIONS

Experimentally Determined Force Systems from Vertically Activated Orthodontic Loops, Authored by Vanderby, Jr. et al. (Oct. 1977), pp. 272–279.

Analysis of Space Closing Springs in Orthodontics, J. Biomechanics, 1974, vol. 7, pp. 21–28.

An evaluation of the torsional moments developed in orthodontic application. An in vitro study, American Journal of Orthodontics and Dentofacial Orthodpedics, Apr. 1994 vol. 105, No. 4; pp. 392–400.

Marketing brochure entitled "F/T Force Torque Sensor System", distributed by ATI Industrial Automation, Peachtree Center 503–D Highway 70 East, Garner North Carolina, 27529 (Jun. 1997).

*Primary Examiner*—Todd E. Manahan
*Attorney, Agent, or Firm*—Maginot, Addison & Moore

[57] ABSTRACT

An orthodontic force measuring apparatus includes a dental replica which includes a first tooth replica and a second tooth replica. The first tooth replica is moveable relative to the second tooth replica. The apparatus also includes an orthodontic appliance secured to both the first tooth replica and the second tooth replica of the dental replica. The apparatus further includes a force measuring device operatively coupled to the first tooth replica. The force measuring device is configured so as to measure force exerted on the first tooth replica by the orthodontic appliance. A method of measuring orthodontic force is also disclosed.

18 Claims, 6 Drawing Sheets

APPARATUS AND METHOD FOR MEASURING ORTHODONTIC FORCE APPLIED BY AN ORTHODONTIC APPLIANCE

TECHNICAL FIELD OF THE INVENTION

The present invention relates generally to a force measurement device, and more particularly to an apparatus and method for measuring orthodontic force applied by an orthodontic appliance.

BACKGROUND OF THE INVENTION

The fields of dentistry and orthodontics attempt to solve the problems associated with proper tooth care and proper tooth location. Orthodontics specifically deals with the moving or turning of abnormally positioned teeth. In this field, it has been commonly accepted that a tooth moves in response to applied forces and torques from an orthodontic appliance. Different orthodontic appliances have been used to provide the necessary mechanical forces to correct improper tooth tipping, rotation, and location.

Each individual patient provides a unique dental structure with respect to tooth orientation and position. Therefore, the application of tooth braces or other orthodontic appliances will not affect all patients uniformly. A significant portion of the patients who require orthodontic appliances are young children and adolescents. This group typically finds the orthodontic appliances to be unsightly and a source of embarrassment. Patients of all ages typically find the orthodontic appliances uncomfortable and desire for them to complete their purpose (i.e. to properly position one's teeth) in the shortest possible amount of time. Hence, a precise measurement technique for determining how the appliance is affecting the position of the teeth will allow increases in the effectiveness of the orthodontic appliance thereby potentially resulting in a shortened time period that the orthodontic appliance must be worn by the patient. Therefore, when a tooth is to be reoriented or otherwise repositioned, it is desirable for clinicians to know the magnitude and direction of forces and torques exerted on the tooth by the orthodontic appliance so that they may better predict the effectiveness of the orthodontic appliance on each tooth. It should be appreciated that clinicians may then use this information to adjust the orthodontic appliance if need be.

Hence, a number of measurement devices have heretofore been designed in an effort to determine the effectiveness of certain orthodontic appliances. For example, measurement devices have heretofore been designed which attempt to measure certain mechanical properties of an orthodontic appliance when it is secured to a number of pedestals or bar-like structures by use of certain types of rigid friction methods. However, such devices have a number of drawbacks associated therewith. For example, use of such rigid friction methods to attach the orthodontic appliance to the pedestals of the heretofore designed measurement device is substantially different than the methods which are utilized to attach the orthodontic appliance in a clinic (i.e. the methods utilized to secure the orthodontic appliance to the patient's teeth) thereby producing potentially inaccurate results. Moreover, heretofore designed measurement devices have typically been able to measure mechanical output of an orthodontic device in only a limited number of axes thereby limiting the value of the measurements obtained by the device.

Accordingly, there remains a need for an accurate measurement device for measuring mechanical output of an orthodontic appliance thereby allowing a clinician to receive more precise data which will allow the clinician to make more informed decisions for the patient's benefit. As a result, increased effectiveness of orthodontic appliances will provide more successful correction of the patient's dental anomalies in a more timely manner thereby reducing the negative connotation associated with the appliances. It will further allow the orthodontic treatment to proceed with greater effectiveness and less clinical monitoring.

Therefore, what is needed is an orthodontic measurement device which overcomes one or more of the above mentioned drawbacks. What is further needed is an orthodontic measurement device which produces more accurate measurement data relative to heretofore designed measurement devices. What is also needed is an orthodontic measurement device which measures orthodontic forces applied by an orthodontic appliance which is customized for individual patients.

SUMMARY OF THE INVENTION

In accordance with a first embodiment of the present invention, there is provided an orthodontic force measurement apparatus. The apparatus includes a dental replica having an orthodontic appliance secured thereto. The apparatus further includes a force measuring device operatively coupled to the dental replica. The force measuring device is configured so as to measure force exerted on the dental replica by the orthodontic appliance.

Pursuant to a second embodiment of the present invention, there is provided a method for measuring orthodontic force. The method includes the step of securing an orthodontic appliance to a dental replica. The method also includes the step of placing a force measuring device in operative contact with the dental replica. The method further includes the step of operating the force measuring device so as the measure force exerted on the dental replica by the orthodontic appliance.

According to a third embodiment of the present invention, there is provided an orthodontic force measuring apparatus. The apparatus includes a dental replica which includes a first tooth replica and a second tooth replica. The first tooth replica is moveable relative to the second tooth replica. The apparatus also includes an orthodontic appliance secured to both the first tooth replica and the second tooth replica of the dental replica. The apparatus further includes a force measuring device operatively coupled to the first tooth replica. The force measuring device is configured so as to measure force exerted on the first tooth replica by the orthodontic appliance.

According to a fourth embodiment of the present invention, there is provided a method of measuring force exerted by an orthodontic appliance. The method includes the step of securing the orthodontic appliance to a dental replica. The method also includes the step of exerting a force on the dental replica with the orthodontic appliance. The method further includes the step of measuring the force exerted on the dental replica by the orthodontic appliance.

It is therefore an object of the present invention to provide a new and useful apparatus and method for measuring orthodontic force.

It is also an object of the present invention to provide an improved apparatus and method for measuring orthodontic force.

It is further an object of the present invention to provide an apparatus and method for measuring orthodontic forces applied by an orthodontic appliance which is customized for individual patients.

It is also an object of the present invention to provide an apparatus and method for measuring orthodontic forces which produces more accurate measurement data relative to heretofore designed measurement devices.

The above and other objects, features, and advantages of the present invention will become apparent from the following description and attached drawings.

DETAILED DESCRIPTION OF THE PREFERRED EMBODIMENT

While the invention is susceptible to various modifications and alternative forms, a specific embodiment thereof has been shown by way of example in the drawings and will herein be described in detail. It should be understood however, that there is no intent to limit the invention to the particular form disclosed, but on the contrary, the intention is to cover all modifications, equivalents, and alternatives falling within the spirit and scope of the invention as defined by the appended claims.

Figure 1:
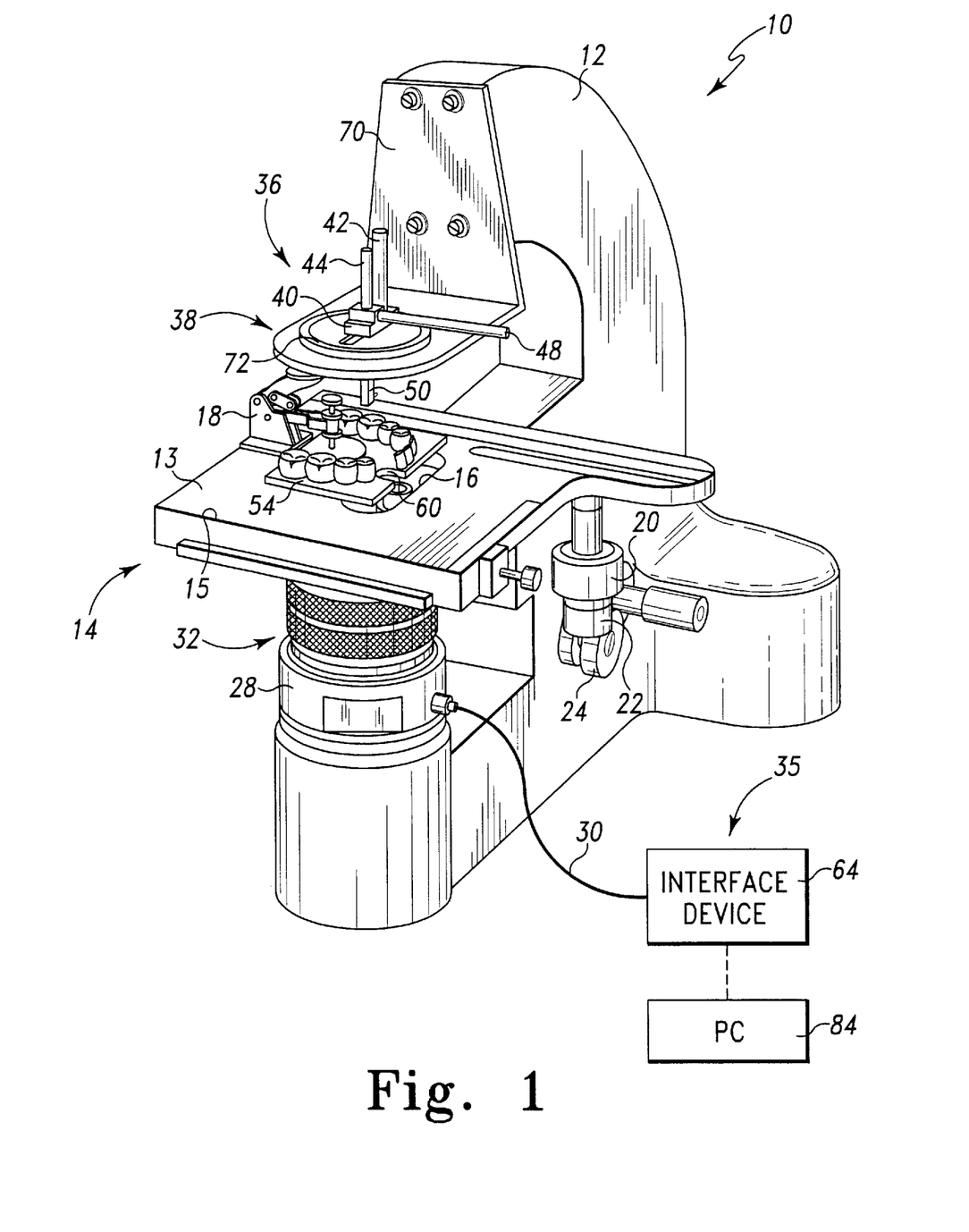
FIG. 1 is a perspective view of an orthodontic force measuring device which incorporates the features of the present invention therein.

Referring now to FIG. 1, there is shown an orthodontic force measuring device 10 which incorporates the features of the present invention therein. The force measuring device 10 includes a tooth position measuring assembly 36, a specimen platform assembly 14, a testing tooth holder 32, and a force sensing assembly 35. The orthodontic force measuring device 10 also includes a base 12 which allows the force measuring device 10 to be positioned on a flat surface such as a tabletop.

Figure 3:
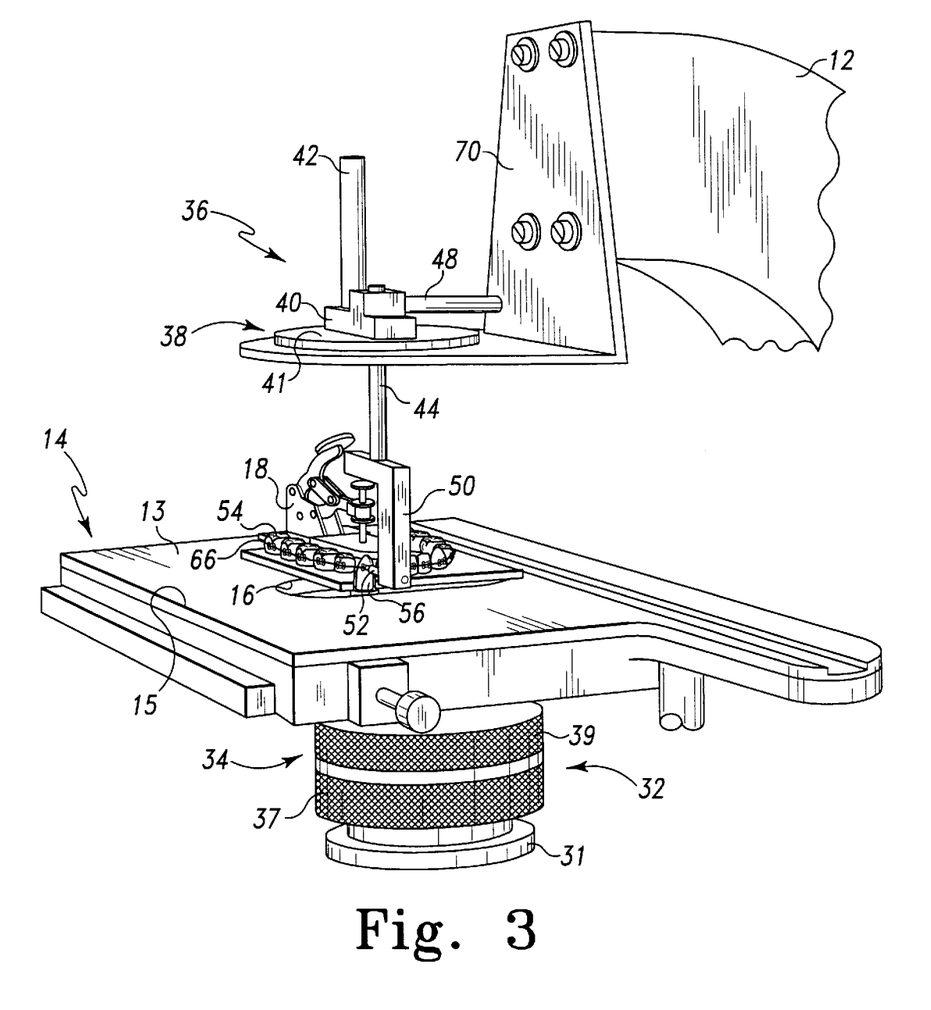
FIG. 3 is an enlarged fragmentary perspective view of the orthodontic force measuring device of FIG. 1 which shows the measurement pin moved relative to its position in FIG. 2 to contact the brace fitting mounted on the dental replica.
Figure 5A:
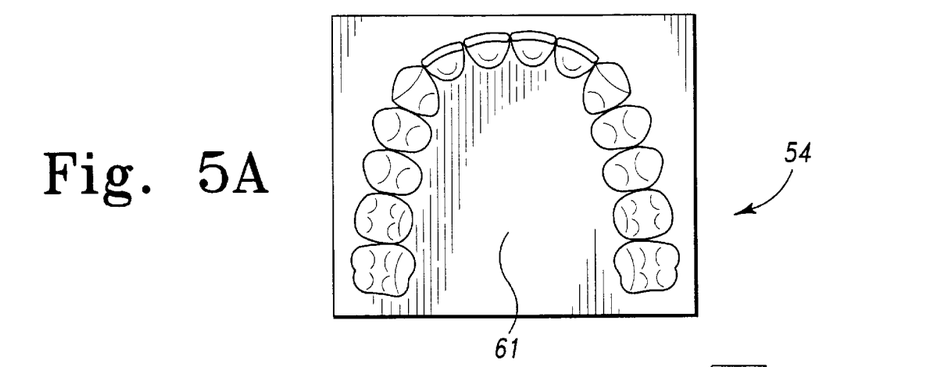
FIGS. 5A–5C are plan views of a dental replica which is utilized in the operation of the orthodontic force measurement device of FIG. 1.
Figure 5B:
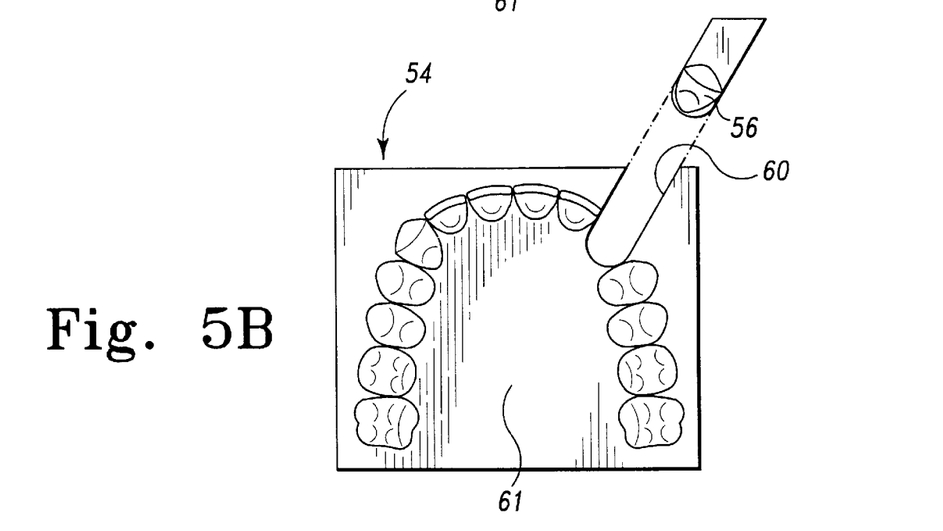

The orthodontic force measuring device 10 is provided to measure the force exerted on a dental replica 54 by an orthodontic appliance such as a set of braces 66 (see FIG. 3). In particular, as shown in FIG. 5A, the dental replica 54 is preferably a replica of the teeth associated with a patient's maxilla or mandible. The dental replica 54 is created by taking a negative mold of the patient's dentition and then creating a positive dental replica by a process well known in the art. The dental replica 54 is then sawed or otherwise cut in order to remove a testing tooth replica 56, thereby creating a tooth gap 60 in a base 61 of the dental replica 54 as shown in FIG. 5B. The removed portion of the dental replica 54 (i.e. the portion which contains the testing tooth replica 56) is then further machined such that only the actual testing tooth replica 56 remains. More specifically, the removed portion of the dental replica 54 is then cut or sanded so as to remove the remainder of the base 61 from around the testing tooth replica 56. As shall be discussed below in greater detail, the force sensing assembly 35 may be utilized to measure the force exerted on the testing tooth replica 56 by an orthodontic appliance such as the set of braces 66.

Figure 4A:
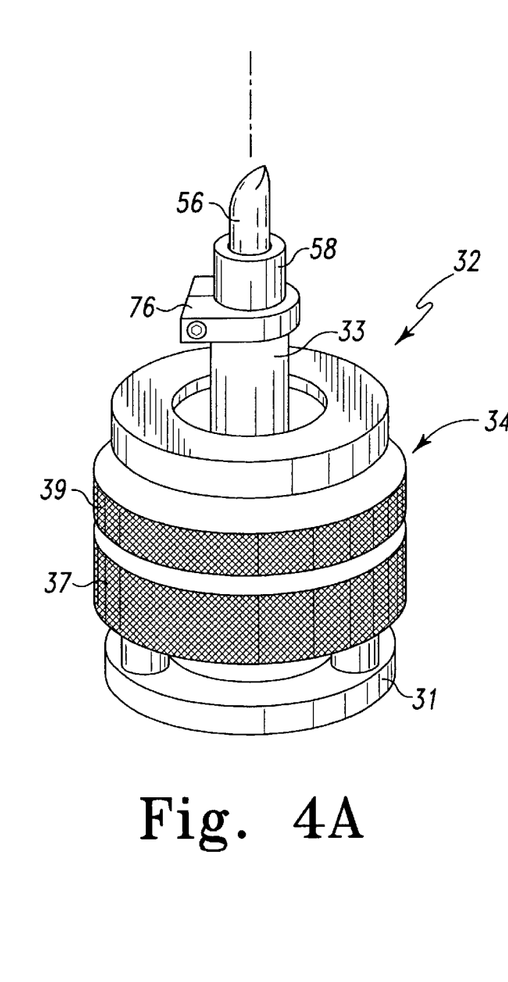
FIGS. 4A–4C are perspective views of the testing tooth holder of the orthodontic force measurement device of FIG. 1 with a tooth replica being shown in multiple locations.
Figure 4B:
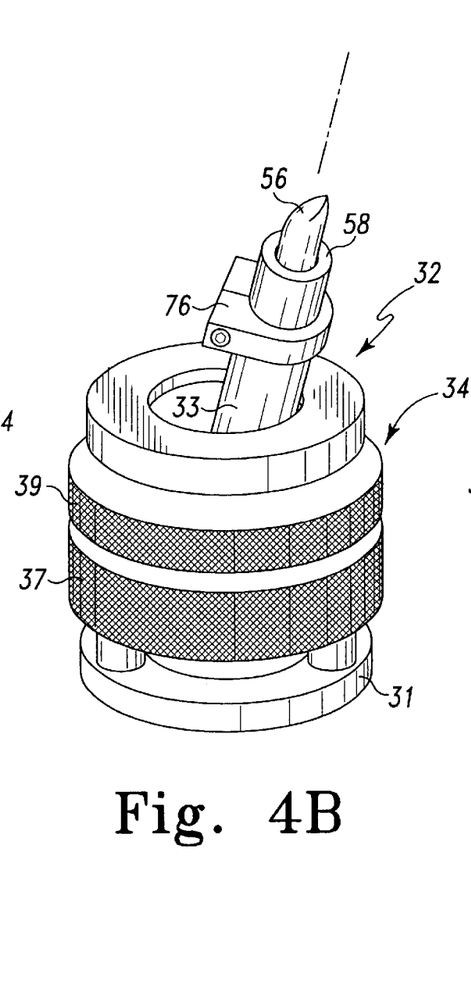
Figure 4C:
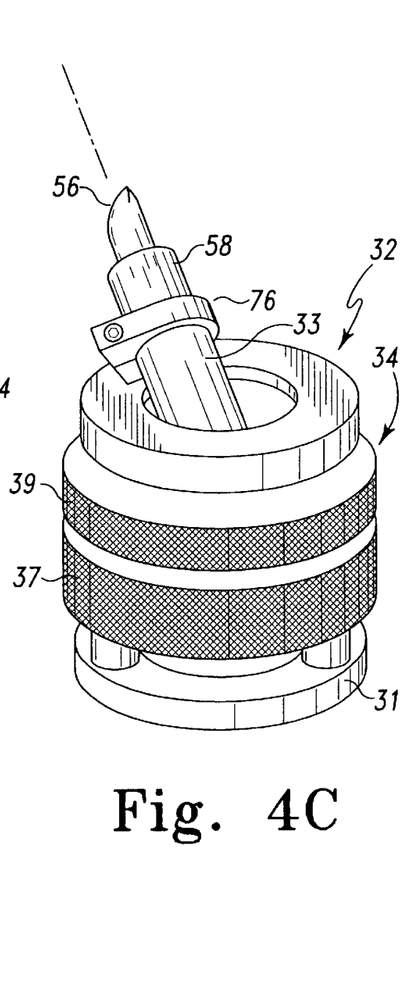

Referring now to FIGS. 4A–4C, there is shown the testing tooth holder 32 in greater detail. The testing tooth holder 32 includes a positioning member 33 which may be placed in any one of numerous positions. In particular, the positioning member 33 is movably secured to a body 37 of the testing tooth holder 32 by a ball socket, slide socket, or the like which provides the positioning member 33 with relatively unlimited freedom of movement in different orientations (e.g. movement in the x-direction and the y-direction) within the physical constraints of the structure of the testing tooth holder 32. It should be appreciated that use of such a ball socket, slide socket, or the like allows the positioning member 33 to assume any one of a variety of angles with respect to the body 37 of the testing tooth holder 32. For example, FIGS. 4A–4C show three exemplary angles at which the positioning member 33 may be positioned; however, as shall be discussed below in greater detail, a locking mechanism 34 allows the positioning member 33 to be positioned and thereafter secured at any location or angle within the physical constraints of the structure of the testing tooth holder 32.

In particular, the positioning member 33 may be selectively locked or otherwise fixed in a desired position by use of the locking mechanism 34 which includes an outer ring 39 which is rotatable relative to the body 37 of the testing tooth holder 32. The locking mechanism 34 further includes an internal clamping mechanism (not shown) which selectively engages the positioning member 33 so as to lock the positioning member 33 in its current position. For example, a clockwise turn of the outer ring 39 of the locking mechanism 34 will cause the clamping mechanism to engage the positioning member 33 thereby locking or otherwise fixing the position of the positioning member 33 of the testing tooth holder 32 in its current location. A subsequent counterclockwise turn of the outer ring 39 of the locking mechanism 34 will disengage the clamping mechanism thereby allowing the positioning member 33 of the testing tooth holder 32 to freely move relative to the body 37 of the testing tooth holder 32.

Figure 6:
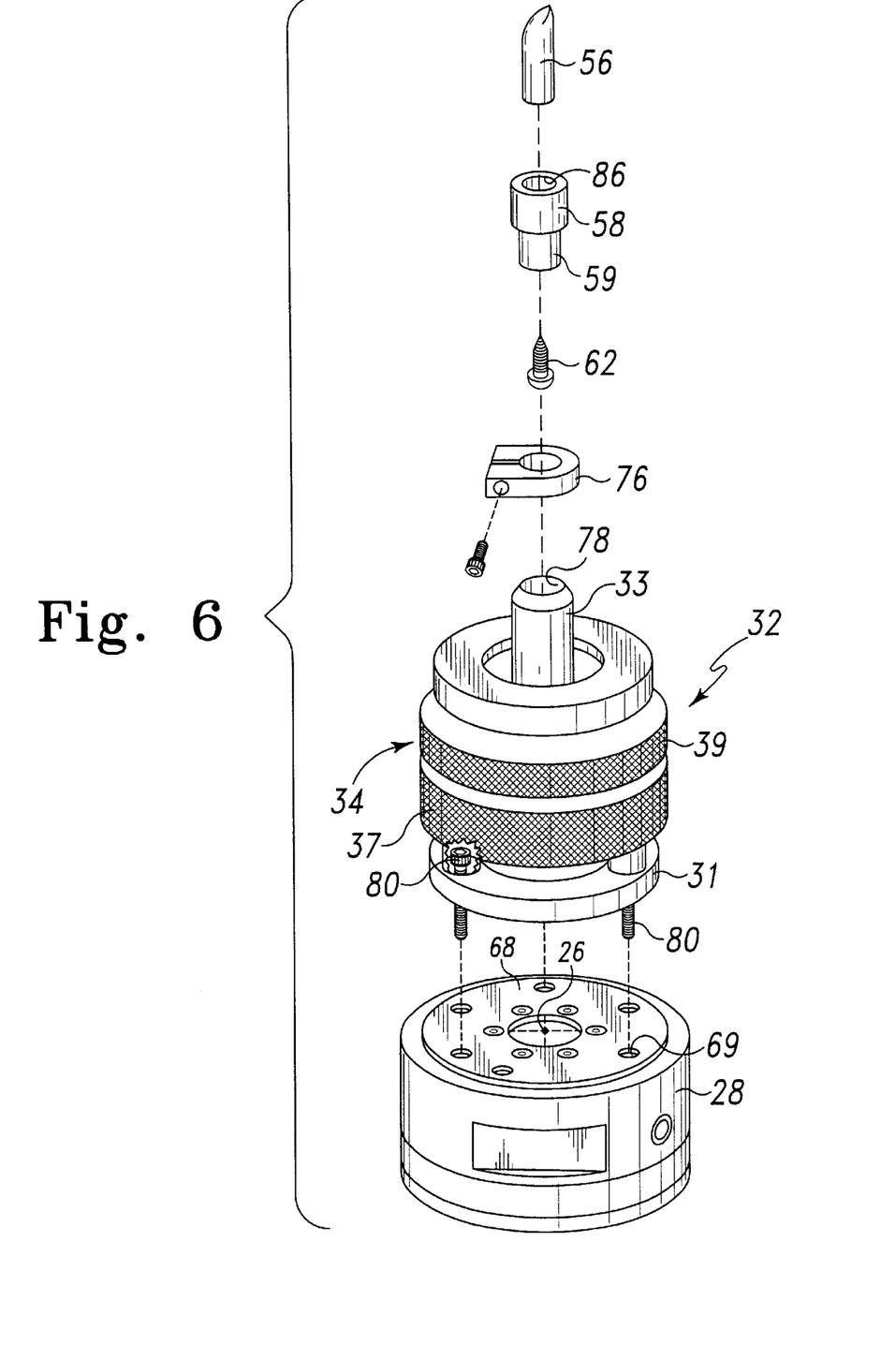
FIG. 6 is an exploded perspective view of the load cell and the testing tooth holder of the orthodontic force measurement device of FIG. 1.

The testing tooth replica 56 is also securable to the testing tooth holder 32. Preferably, as shown in FIG. 6, the testing tooth replica 56 is secured to the positioning member 33 by the use of a tooth retainer 58. In particular, the testing tooth replica 56 is received into a retaining bore 86 defined in the tooth retainer 58. The testing tooth replica 56 is secured in the retaining bore 86 of the tooth retainer 58 by advancing a screw 62 through a hole (not shown) in the underside of the tooth retainer 58 which thereafter threadingly engages the testing tooth replica 56. It should be appreciated that slight modification to the tooth replica 56 may be required in order to secure the testing tooth replica 56 to the tooth retainer 58. For example, a short extension (not shown) may need to be secured to replica 56 in order to allow the tooth replica 56 to extend fully out of the retaining bore 86. Such an extension is preferably constructed of a material which is capable of having the screw 62 threadingly engaged therein. Moreover, such an extension may be integrally molded with the testing tooth replica 56 or may alternatively be provided as a separate component which is adhesively or otherwise secured to the testing tooth replica 56.

The tooth retainer 58, including the testing tooth replica 56 secured thereto, is securable to the positioning member 33 of the testing tooth holder 32. As shown in FIG. 6, the tooth retainer 58 includes a lower portion 59 that has an outer surface that is slightly smaller in diameter than the inner diameter of a retaining bore 78 of the positioning member 33 thereby allowing the tooth retainer 58 to telescopingly engage the positioning member 33. The tooth retainer 58 may then be firmly held in rigid contact with the positioning member 33 by use of a clamp such as a circular clamp 76. The circular clamp 76 includes a bolt which may be tightened or loosened to likewise tighten or loosen the grip of the circular clamp 76 on the tooth retainer 58 and the positioning member 33. The circular clamp 76 is placed over the joint between the tooth retainer 58 and positioning member 33 and then tightened so as to hold the tooth retainer 58 and the positioning member 33 in their current position relative to one another. The circular clamp 76 may likewise be loosened in order to move the tooth retainer 58 and the positioning member 33 relative to one another. It should be appreciated that such use of the circular clamp 76 allows the tooth retainer 58 to be selectively rotated relative to the positioning member 33 to allow the testing tooth replica 56 to be positioned in a desired orientation.

Again referring to FIG. 6, the body of the testing tooth holder 32 is attached to an input plate 68 of a force/torque sensor 28 of the force sensing assembly 35. The testing tooth holder 32 is preferably fastened to the input plate 68 with the use of a plurality of bolts 80 which pass through a fastening plate 31 of the testing tooth holder 32 and thereafter threadingly engage a number of fastening apertures 69 defined in the input plate 68 so as to secure the testing tooth holder 32 to input plate 68 of the force/torque sensor 28. As shall be discussed below in greater detail, mounting the testing tooth holder 32 to the force/torque sensor 28 in such a manner allows the force/torque sensor 28 to monitor or otherwise detect forces exerted on the testing tooth 56 by an orthodontic appliance such as the braces 66.

As shown in FIG. 1, the force sensing assembly 35 includes the force/torque sensor 28 and an interface device 64. The force sensing assembly 35 is provided to measure or otherwise detect forces (e.g. linear forces and torques) exerted on the testing tooth replica 56 when the testing tooth replica 56 is secured in the tooth retainer 58 (see FIG. 2). In particular, when a force, such as an orthodontic force generated by the braces 66, is exerted on the testing tooth replica 56, the force is transferred to the input plate 68 of the force/torque sensor 28 via a mechanical path which includes the tooth retainer 58 and the testing tooth holder 32 thereby causing deflection of the input plate 68. From the above discussion, it should be appreciated that the force sensing assembly 35 is operatively coupled to the dental replica 54. What is meant herein by the term "operatively coupled" in regard to the force sensing assembly 35 is that the force sensing assembly 35 is either directly or indirectly mechanically coupled to a component such that forces exerted on the component may be detected by the force sensing assembly 35. For example, as shown in FIGS. 3 and 6, the force sensing assembly 35 is operatively coupled to the testing tooth replica 56 of the dental replica 54 since forces exerted on the testing tooth replica 56 by the braces 66 are detected by the force/torque sensor 28 when such forces are mechanically transferred to the input plate 68 via a mechanical path which includes the tooth retainer 58 and the testing tooth holder 32. Likewise, the force sensing assembly 35 is operatively coupled to the testing tooth holder 32 since the testing tooth holder 32 is directly coupled to the input plate 68 (see FIG. 6) of the force/torque sensor such that forces generated by the braces 66 and exerted on the testing tooth holder 32 (via the testing tooth replica 56 and the tooth holder 58) are detected by the force/torque sensor 28 when such forces are mechanically transferred to the input plate 68 via the testing tooth holder 32.

The force/torque sensor 28 includes a transducer which converts the forces exerted on the input plate 68 into an output signal in the form of an amplified analog voltage which is indicative of the forces exerted on the input plate 68. Such an output signal is communicated via a signal line 30 to the interface device 64. The interface device 64 contains an A/D converter which digitizes the amplified analog voltages so as to produce a digital data stream which may be, for example, output via a signal line to a computing device such as a personal computer 84 such that the information associated with the digital data stream (i.e. the magnitude and direction of the forces generated by the braces 66) may be displayed on a display monitor (not shown) or manipulated as discussed below.

The force sensing assembly 35 may be any known force sensing assembly which is capable of sensing or otherwise detecting forces exerted on the testing tooth replica 56 in a manner which fits the design needs of a given orthodontic force measuring device 10. Preferably, the force sensing assembly 35 is capable of simultaneously sensing linear forces exerted on the testing tooth replica 56 in all three directions (i.e. each of the x-, y-, and z-directions) along with also sensing torques exerted on the testing tooth replica 56 in all three directions (i.e. each of the x-, y-, and z-directions). One such force sensing assembly which may be utilized as the force sensing assembly 35 of the present invention is a Force/Torque Sensor System which is commercially available from ATI Industrial Automation of Garner, N.C.

Figure 2:
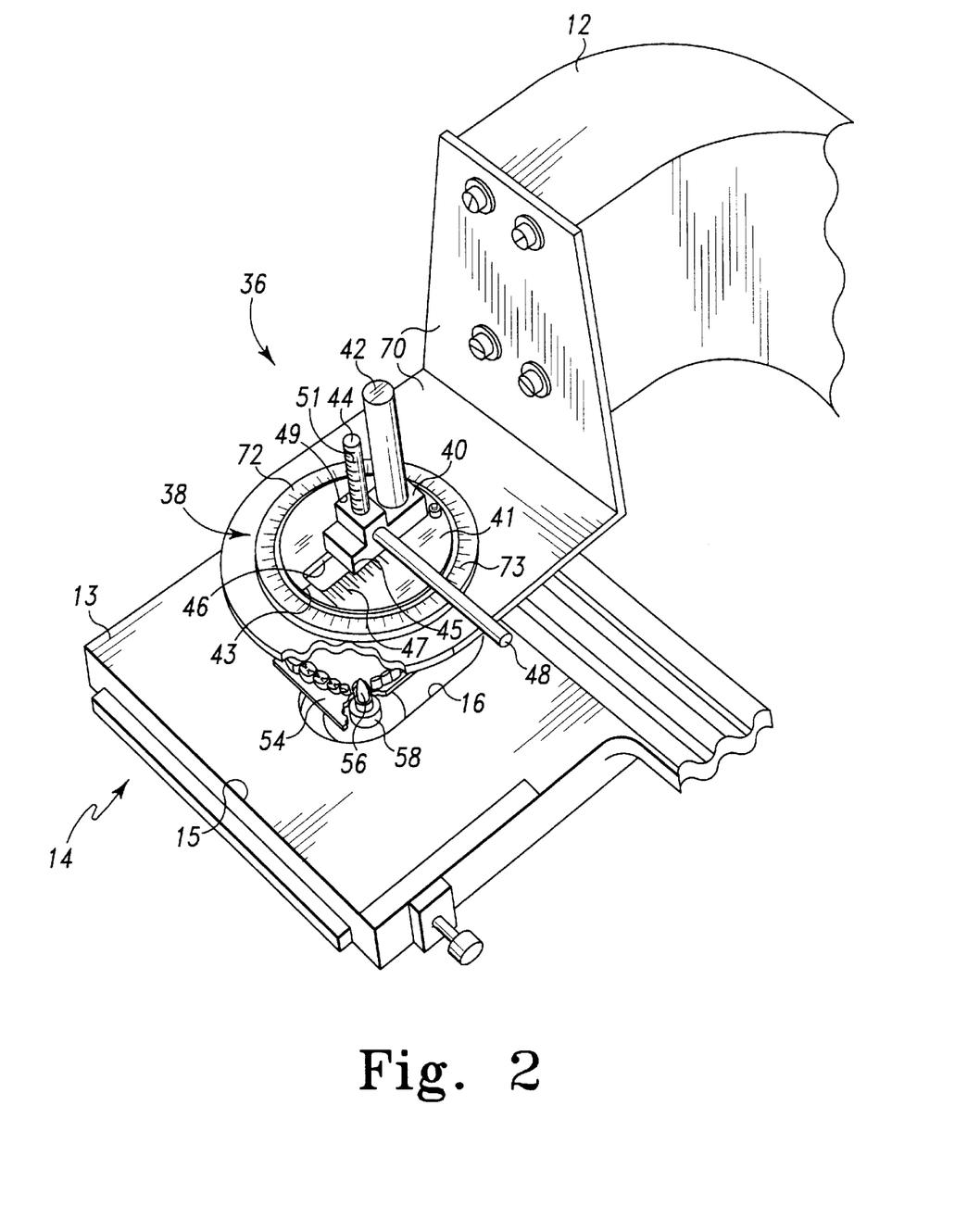
FIG. 2 is an enlarged fragmentary perspective view of the orthodontic force measuring device of FIG. 1.
Figure 5C:
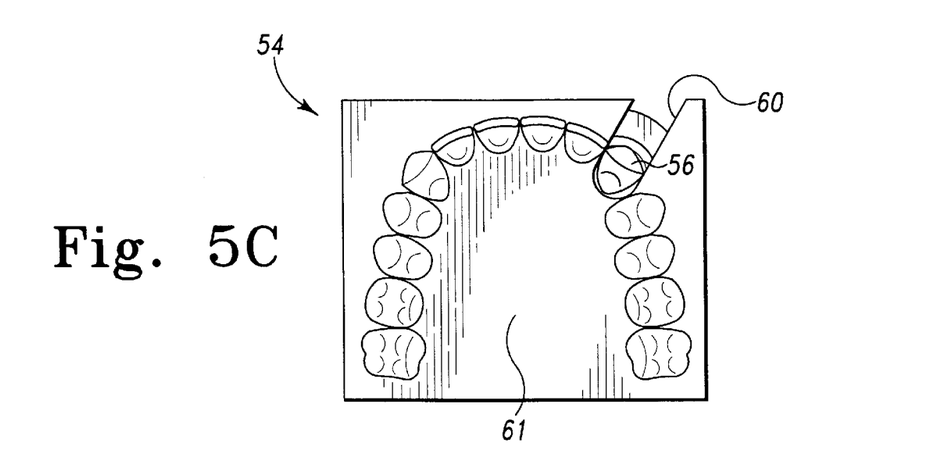

As shown in FIG. 1, the testing tooth holder 32 and force/torque sensor 28 are secured to the base 12 of the orthodontic force measuring device 10 so as to be positioned below the specimen platform assembly 14. The specimen platform assembly 14 is secured to the base 12 and includes a substantially horizontal holding plate 13. The horizontal plate 13 of the specimen platform assembly 14 has a receiving aperture 16 defined therein which allows the testing tooth replica 56 to be advanced therethrough when the testing tooth replica 56 is positioned in the tooth retainer 58. Advancing the testing tooth replica 56 in such a manner allows it to be positioned in its original (i.e. uncut) orientation relative to the other teeth of the dental replica 54. In particular, the remaining portion of the dental replica 54 is secured to the upper surface 15 of the horizontal plate 13 by a holding clamp 18. The clamp 18 selectively applies pressure to the base 61 of the dental replica 56 to secure it in rigid contact with the horizontal plate 13 of the specimen platform assembly 14. Hence, the clamp 18 and the horizontal plate 13 collectively define a tooth holder for holding the portion of the dental replica 54 from which the testing tooth replica 56 was cut. The horizontal plate 13 of the specimen platform assembly 14 may be moved in the x-, y-, and z-directions by use of a number of knobs 20, 22, and 24, respectively, so as to align the tooth gap 60 of the dental replica 54 with the testing tooth replica 56 as it extends up through the receiving aperture 16 in the horizontal plate 13 as shown in FIGS. 2 and 5C.

Once the testing tooth replica 56 is received into the tooth gap 60, the testing tooth replica 56 may be further adjusted such that the position and orientation of the testing tooth replica 56 closely resembles or matches the orientation of the tooth it represents in the patient's mouth. In particular, the position and orientation of the testing tooth replica 56 may be adjusted by use of the locking mechanism 34, the platform assembly 14, and the circular clamp 76 (as discussed above) such that the position and orientation of the testing tooth replica 56 closely resembles or matches the orientation of the tooth it represents in the patient's mouth. Adjustment of the position and orientation of the testing tooth replica may be further accomplished by rotating the tooth retainer 58 to achieve the proper rotation of the testing tooth replica 56. Once the proper position and orientation of the testing tooth replica 56 are achieved, the testing tooth replica 56 may be held in place by tightening the outer ring 39 of the locking mechanism 34 and also tightening the circular clamp 76. To ensure that the testing tooth replica 56 is properly aligned, the negative mold of the patient's dentition which was utilized to construct the dental replica 54 may be placed over both the dental replica 54 and testing tooth replica 56. A snug fit by the negative mold onto both the testing tooth replica 56 and dental replica 54 indicates that the testing tooth replica 56 has been repositioned and reoriented properly within the dental replica 54.

When both the testing tooth replica 56 and the remaining dental replica 54 are secured in a proper position and orientation relative to one another, the braces 66 or other orthodontic appliances are then attached to the dental replica 54 and testing tooth replica 56 as shown in FIG. 3. The orthodontic appliance is manipulated to cause forces and torques to be applied to the testing tooth replica 56. The forces and torques are then translated through the testing tooth replica 56, the tooth retainer 58, and the testing tooth holder 32 to the input plate 68 of the force/torque sensor 28. The forces and torques exerted on the testing tooth replica 56 are then detected by the force/torque sensor 28 such that the force/torque information may then be output on the signal line 30 to the interface device 64.

Force measurements detected by the force/torque sensor 28 (see FIGS. 1 and 6) are indicative of the force generated by the braces 66 as detected at a location which is remote from the testing tooth replica 56. In particular, forces detected by the force/torque sensor 28 are indicative of the magnitude and direction of the forces generated by the braces 66 as exerted on a measurement location 26 (see FIG. 6) which is approximately the center of the input plate 68 of the force/torque sensor 28. In order to determine the magnitude and direction of the forces being exerted on the testing tooth replica 56 itself by the braces 66, the magnitude and direction of the detected forces (i.e. the magnitude and direction of the forces exerted on the measurement location 26) must be extrapolated to provide the desired force measurement values.

Accordingly, FIG. 2 shows the tooth position measuring assembly 36 which is secured to the base 12 so as to be positioned above the specimen platform assembly 14 and the dental replica 54. The tooth position measuring assembly 36 contains an attachment plate 70, a rotation plate assembly 38, a sliding member 40, a measurement rod 44 having a lower portion 50 (see also FIG. 3), a contact pin 52, and two hand screws 42 and 48. The attachment plate 70 is substantially L-shaped having a first portion which extends vertically and is secured to the base 12 and a second portion which extends horizontally and supports the rotation plate assembly 38. The rotation plate assembly 38 lies parallel to and immediately above the attachment plate 70. The rotation plate assembly 38 consists of a circular-shaped rotating plate 41 having a outer ring 72 positioned around the periphery thereof. The outer ring 72 is non-movably secured to the attachment plate 70 and has a graduated scale 73 defined therein. The rotating plate 41 is rotatable relative to the outer ring 72 and includes an indicator line 43 which cooperates with the graduated scale 73 of the outer ring 72 so as to indicate the angle of the rotating plate 41, and hence the measurement rod 44 and the contact pin 52 (see FIG. 3), relative to the outer ring 72.

The sliding member 40 is preferably a metal block which is free to slide linearly within a slot 46 defined in the rotating plate 41. In particular, the hand screw 42 may be loosened so as to allow the sliding member 40 to slide freely within the slot 46 to a desired location. Once positioned in the desired location, the hand screw 42 may be tightened thereby locking the sliding member 40 in its desired location. The sliding member 40 further includes a forward edge 45 which cooperates with a graduated scale 47 defined in the rotating plate 41 so as to indicate the lateral position of the sliding member 40 (and hence the measurement rod 44 and the contact pin 52) relative to the rotating plate 41.

The measurement rod 44 is received through the sliding member 40 and may be utilized to adjust the position of the contact pin 52 upwardly and downwardly. In particular, the hand screw 48 may be loosened so as to allow the measurement rod 44 to slide freely upwardly and downwardly relative to the sliding member 40 to a desired location. Once positioned in the desired location, the hand screw 48 may be tightened so as to retain the measurement rod 44 in its desired location. The sliding member 40 further includes a top edge 49 which cooperates with a graduated scale 51 defined in the measurement rod 44 so as to indicate the vertical position of the measurement rod 44 (and hence the contact pin 52) relative to the sliding member 40.

As shown in FIG. 3, the contact pin 52 is secured to the lower portion 50 of the measurement rod 44. The contact pin 52 may be height adjusted by loosening the hand screw 48 and adjusting the measurement rod 44. The contact pin 52 may be horizontally translated by loosening the hand screw 42 and sliding the sliding member 40 within the slot 46 (see FIG. 2). Further, rotation of the rotating plate 41 allows the sliding member 40, the measurement rod 44, and hence the contact pin 52 to be likewise rotated as seen in FIG. 3. The contact pin 52 may be adjusted in the above described manner in order to position the contact pin 52 in contact with the portion of the braces 66 that is secured to the testing tooth replica 56.

Once the contact pin 52 is positioned in contact with the portion of the braces 66 that is secured to the testing tooth replica 56, the hand screws 42 and 48 may be tightened so as to lock or otherwise secure the contact pin 52 into a position in which the contact pin 52 contacts the portion of the braces 66 secured to the testing tooth replica 56. Thereafter, the height location, horizontal location, and rotational orientation of the contact pin 52 may then be determined by use of the graduated scales 43, 47, and 51 associated with the tooth position measuring assembly 36.

It should be appreciated that the position of the contact pin 52 is utilized to determine the force being exerted on the testing tooth replica 56 by the braces 66. In particular, as discussed above, orthodontic forces generated by the braces 66 are detected by the force/torque sensor 28 (see FIGS. 1 and 6). However, the forces detected by the force/torque sensor 28 are indicative of the magnitude and direction of the orthodontic force as exerted at the measurement location 26 of the force/torque sensor 28 (see FIG. 6). The actual forces detected by the force/torque sensor 28, along with the distance of the testing tooth replica 56 from the measurement location 26, may be utilized in mathematical calculations associated with known force translation models to determine the magnitude and direction of the orthodontic forces actually being exerted on the testing tooth replica 56. Accordingly, the personal computer 84 preferably executes software which performs the mathematical calculations associated with the force translation models when the necessary data (i.e. the force detected by the force/torque sensor 28 and the distance from the testing tooth replica 56 to the measurement location 26) is entered into the personal computer 84.

In operation, in order to determine the orthodontic forces which will be exerted on a patient's teeth when an orthodontic appliance such as braces are placed on the patient's teeth, a dental replica of the teeth associated with a patient's maxilla or mandible is first created. The dental replica 54 is created by taking a negative mold of the patient's dentition and then creating a positive dental replica by a process well known in the art. The dental replica 54 is then sawed or otherwise cut in order to remove the testing tooth replica 56 thereby creating the tooth gap 60 in the base 61 of the dental replica 54 as shown in FIG. 5B. The removed portion of the dental replica 54 (i.e. the portion which contains the testing tooth replica 56) is then further machined such that only the actual testing tooth replica 56 remains. More specifically, the removed portion of the dental replica 54 is then cut or sanded so as to remove the remainder of the base 61 from around the testing tooth replica 56. If needed an extension (not shown) is then affixed to the testing tooth replica 56 by use of an adhesive or other material.

The testing tooth replica 56 is then secured to the positioning member 33 by the use of a tooth retainer 58. In particular, the testing tooth replica 56 is received into the retaining bore 86 defined in the tooth retainer 58 and thereafter held in the tooth retainer 58 by use of the screw 62. As discussed above, a short extension (not shown) may need to be secured to testing tooth replica 56 in order to allow the tooth replica 56 to extend fully out of the retaining bore 86. The tooth retainer 58, including the testing tooth replica 56 secured thereto, are then secured to the positioning member 33 of the testing tooth holder 32 by use of the circular clamp 76. The bolt associated with the circular clamp 76 may be tightened or loosened to likewise tighten or loosen the grip of the circular clamp 76 on the tooth retainer 58 and the positioning member 33 so as to allow the tooth retainer 58 (and hence the testing tooth replica 56) to be secured in a desired orientation.

The remaining portion of the dental replica 54 (i.e. the portion of the dental replica from which the testing tooth replica 56 was removed) is then secured to the upper surface 15 of the horizontal plate 13 by use of the clamp 18. The horizontal plate 13 of the specimen platform assembly 14 may then be moved in the x-, y-, and z-directions by use of a number of knobs 20, 22, and 24, respectively, so as to advance the testing tooth replica 56 through the receiving aperture 16. Thereafter, the testing tooth replica 56 is advanced into the tooth gap 60 by further use of the knobs 20, 22, and 24 as the testing tooth replica 56 extends up through the receiving aperture 16 in the horizontal plate 13 (see FIGS. 2 and 5C).

Once tooth replica 56 is received into the tooth gap 60, the position and orientation of the testing tooth replica 56 is then further adjusted such that the position and orientation of the testing tooth replica 56 closely resembles or matches the position and orientation of the tooth it represents in the patient's mouth. In particular, the position and orientation of the testing tooth replica 56 may be adjusted by use of the locking mechanism 34 and the circular clamp 76 as discussed above such that the position and orientation of the testing tooth replica 56 closely resembles or matches the position and orientation of the tooth it represents in the patient's mouth. Once the proper position and orientation of the testing tooth replica 56 is achieved, the testing tooth replica 56 may be held in place by tightening the outer ring 39 of the locking mechanism 34 and the circular clamp 76. To ensure that the testing tooth replica 56 is properly aligned, the negative mold of the patient's dentition which was utilized to construct the dental replica 54 may be placed over both the dental replica 54 and testing tooth replica 56. A snug fit by the negative mold onto both the testing tooth replica 56 and dental replica 54 indicates that the testing tooth replica 56 has been repositioned and reoriented properly within the dental replica 54.

When both the testing tooth replica 56 and the remaining portion of the dental replica 54 are secured in a proper position and orientation relative to one another, the braces 66 or other orthodontic appliances are then attached to the dental replica 54 and testing tooth replica 56 as shown in FIG. 3. The orthodontic appliance causes forces and torques to be applied to the testing tooth replica 56. The forces and torques are then translated through the testing tooth replica 56, the tooth retainer 58, and the testing tooth holder 32 to the input plate 68 of the force/torque sensor 28. The forces and torques exerted on the testing tooth replica 56 are then detected by the force/torque sensor 28 such that an output signal in the form of an analog voltage is output on the signal line 30 to the interface device 64. The interface device 64 in turn produces a digital data stream which is output, for example, via a signal line to the personal computer 84 such that the information associated with the digital data stream (i.e. the magnitude and direction of forces generated by the braces 66) may be displayed on a display monitor (not shown) or manipulated by software associated with the personal computer 84 as discussed below.

The tooth position measuring assembly 36 is then operated to determine the distance from the testing tooth replica 56 to the measuring location 26 of the force/torque sensor 28. In particular, the contact pin 52 may be height adjusted by loosening the hand screw 48 and adjusting the measurement rod 44. The contact pin 52 may be horizontally translated by loosening the hand screw 42 and sliding the sliding member 40 within the slot 46. Further, rotation of the rotating plate 41 allows the sliding member 40, the measurement rod 44, and hence the contact pin 52 to be likewise rotated as seen in FIG. 3. Hence, the contact pin 52 may be adjusted in the above described manner in order to position the contact pin 52 in contact with the portion of the braces 66 that is secured to the testing tooth replica 56.

Once the contact pin 52 is positioned in contact with the portion of the braces 66 that is secured to the testing tooth replica 56, the hand screws 42 and 48 may be tightened so as to lock or otherwise secure the contact pin 52 into a position in which the contact pin 52 contacts the portion of the braces 66 secured to the testing tooth replica 56. Thereafter, the height location, horizontal location, and rotational orientation of the contact pin 52 may then be determined by use of the graduated scales associated with the tooth position measuring assembly 36.

As discussed above, the position of the contact pin 52 is utilized to determine the force being exerted on the testing tooth replica 56 by the braces 66. In particular, orthodontic forces generated by the braces 66 are detected by the force/torque sensor 28; however, the forces sensed by the force/torque sensor 28 are indicative of the magnitude and direction of the orthodontic force as exerted at the measurement location 26 of the force/torque sensor 28. Both the actual force detected by the force/torque sensor 28, along with the distance from the testing tooth replica 56 to the measurement location 26, are input into the personal computer 84 such that known force translation models may be utilized to determine the magnitude and direction of the forces and torques actually being exerted on the testing tooth replica 56 by the orthodontic appliance (i.e. the braces 66).

While the invention has been illustrated and described in detail in the drawings and foregoing description, such illustration and description is to be considered as exemplary and not restrictive in character, it being understood that only preferred embodiments have been shown and described and that all changes and modifications that come within the spirit of the invention are desired to be protected.

There are a plurality of advantages of the present invention arising from the various features of the orthodontic force measurement device described herein. It will be noted that alternative embodiments of the orthodontic force measurement device of the present invention may not include all of the features described yet still benefit from at least some of the advantages of such features. Those of ordinary skill in the art may readily devise their own implementations of the orthodontic force measurement device that incorporate one or more of the features of the present invention and fall within the spirit and scope of the present invention as defined by the appended claims.

What is claimed is:

1. An orthodontic force measuring apparatus, comprising:
    a dental replica having an orthodontic appliance secured thereto; and
    a force measuring device operatively coupled to said dental replica, wherein said force measuring device is configured to measure force exerted on said dental replica by said orthodontic appliance,
    wherein said dental replica includes a first tooth replica and a second tooth replica with said first tooth replica being movable relative to said second tooth replica,
    wherein said first tooth replica is coupled to said second tooth replica by said orthodontic appliance, and
    wherein said force measuring device is operatively coupled to said first tooth replica so as to measure force exerted on said first tooth replica by said orthodontic appliance.

2. The apparatus of claim 1 further comprising a tooth holder, wherein:
    said first tooth replica is secured to said tooth holder, and
    said force measuring device is operatively coupled to said tooth holder so as to measure force exerted on said tooth holder by said orthodontic appliance.

3. The apparatus of claim 2, wherein:
    said force measuring device includes a force transducer, and
    said tooth holder is secured to an input of said force transducer.

4. The apparatus of claim 1 further comprising a first tooth holder and a second tooth holder, wherein:
    said first tooth replica is secured to said first tooth holder,
    said second tooth replica is secured to said second tooth holder,
    said first tooth holder is movable relative to said second tooth holder, and
    said force measuring device is operatively coupled to said first tooth holder so as to measure force exerted on said first tooth replica by said orthodontic appliance.

5. The apparatus of claim 4, wherein:
    said second tooth holder includes (i) a holding plate, and (ii) a holding clamp, and
    said second tooth replica is non-movably secured to said holding plate by said holding clamp.

6. The apparatus of claim 5, wherein:
    said holding plate has a receiving aperture defined therein, and
    said first tooth holder is positionable relative to said second tooth holder such that said first tooth replica is received through said receiving aperture, whereby said first tooth replica is positioned proximate to said second tooth replica when said first tooth replica is received through said receiving aperture.

7. The apparatus of claim 1, further comprising a tooth position measuring device, wherein said tooth position measuring device is configured to measure the position of said first tooth replica relative to a predetermined measurement location.

8. The apparatus of claim 7, wherein:
    said force measuring device includes a force transducer having an input plate associated therewith, and
    a portion of said input plate defines said predetermined measurement location.

9. A method of measuring orthodontic force, comprising the steps of:
    securing an orthodontic appliance to a dental replica;
    placing a force measuring device in operative contact with said dental replica; and
    operating said force measuring device so as to measure force exerted on said dental replica by said orthodontic appliance,
    wherein said dental replica includes a first tooth replica and a second tooth replica with said first tooth replica being movable relative to said second tooth replica,
    wherein said first tooth replica is coupled to said second tooth replica by said orthodontic appliance, and
    wherein said step of operating said force measuring device so as to measure force exerted on said dental replica by said orthodontic appliance includes the step of operating said force measuring device so as to measure force exerted on said first tooth replica by said orthodontic appliance.

10. The method of claim 9, further comprising the step of securing said first tooth replica to a tooth holder, wherein:
    said step of operating said force measuring device so as to measure force exerted on said dental replica by said orthodontic appliance includes the step of operating said force measuring device so as to measure force exerted on said tooth holder by said orthodontic appliance.

11. The method of claim 9, wherein:
    said force measuring device includes a force transducer, and
    said step of placing said force measuring device in operative contact with said dental replica includes the step of securing said tooth holder to an input of said force transducer.

12. The method of claim 9, wherein:
    said force measuring device includes a force transducer, and
    said step of operating said force measuring device so as to measure force exerted on said dental replica by said orthodontic appliance includes the steps of (i) determining output from said force transducer, and (ii) generating a calculated force value based on said output from said force transducer.

13. An orthodontic force measuring apparatus, comprising:
   a dental replica which includes a first tooth replica and a second tooth replica with said first tooth replica being moveable relative to said second tooth replica;
   an orthodontic appliance secured to both said first tooth replica and said second tooth replica of said dental replica; and
   a force measuring device operatively coupled to said first tooth replica, wherein said force measuring device is configured to measure force exerted on said first tooth replica by said orthodontic appliance.

14. The apparatus of claim 13 further comprising a first tooth holder and a second tooth holder, wherein:
   said first tooth replica is secured to said first tooth holder,
   said second tooth replica is secured to said second tooth holder,
   said first tooth holder is movable relative to said second tooth holder, and
   said first tooth holder is operatively coupled to an input of a force transducer so as to measure force exerted on said first tooth replica by said orthodontic appliance.

15. The apparatus of claim 14, wherein:
   said second tooth holder includes (i) a holding plate, and (ii) a holding clamp, and
   said second tooth replica is non-movably secured to said holding plate by said holding clamp.

16. The apparatus of claim 15, wherein:
   said holding plate has a receiving aperture defined therein, and
   said first tooth holder is positionable relative to said second tooth holder such that said first tooth replica is received through said receiving aperture, whereby said first tooth replica is positioned proximate to said second tooth replica when said first tooth replica is received through said receiving aperture.

17. The apparatus of claim 13, further comprising a tooth position measuring device, wherein said tooth position measuring device is configured to measure the position of said first tooth replica relative to a predetermined measurement location.

18. The apparatus of claim 17, wherein:
   said force measuring device includes a force transducer having an input plate associated therewith, and
   a portion of said input plate defines said predetermined measurement location.

* * * * *